(12) United States Patent
Sugimura et al.

(10) Patent No.: US 7,384,633 B2
(45) Date of Patent: Jun. 10, 2008

(54) HUMAN TYPE ANTIHUMAN IGE RECEPTOR ANTIBODY AND FRAGMENT

(75) Inventors: Kazuhisa Sugimura, Kagoshima-ken (JP); Toshihiro Nakashima, Kumamoto-ken (JP); Masaharu Torikai, Kumamoto-ken (JP)

(73) Assignee: Judicial Foundation the Chemo-Sero-Therapeutic Res., Kumamoto-ken (JP)

( * ) Notice: Subject to any disclaimer, the term of this patent is extended or adjusted under 35 U.S.C. 154(b) by 437 days.

(21) Appl. No.: 10/484,206

(22) PCT Filed: Jul. 18, 2002

(86) PCT No.: PCT/JP02/07283

§ 371 (c)(1),
(2), (4) Date: Jan. 20, 2004

(87) PCT Pub. No.: WO03/008584

PCT Pub. Date: Jan. 30, 2003

(65) Prior Publication Data

US 2005/0170451 A1 Aug. 4, 2005

(30) Foreign Application Priority Data

Jul. 19, 2001 (JP) .............................. 2001-219990

(51) Int. Cl.
*A61K 39/395* (2006.01)
(52) U.S. Cl. ............................... 424/142.1; 424/133.1; 424/135.1; 424/144.1; 424/805
(58) Field of Classification Search ...................... None
See application file for complete search history.

(56) References Cited

U.S. PATENT DOCUMENTS 6,011,138 A * 1/2000 Reff et al. ............. 530/388.22

FOREIGN PATENT DOCUMENTS

| EP | 0 499 112 A | 8/1992 |
|---|---|---|
| JP | 05-252988 A | 10/1993 |
| JP | 09-191886 A | 7/1997 |

OTHER PUBLICATIONS

Vaughan et al., Nature Biotechnology, 1998, 16:535.-539.*
Novak et al., Curr. Opin. Immunol., 2001, 13:721-726.*
Janeway et al., Immunobiology, 3rd edition, Garland Press, 1997, pp. 3:1-3:38.*
Fiebiger et al., Curr. Opin. Immunol. 1996, 8:784-789.*
Riske et al., J. Biol. Chem., 1991, 266:11245-11251.*
Garman, Scott et al., "Structure of the Fc fragment of human IgE bound to its high-affinity receptor FcεRiα", Nature, vol. 406, Jul. 20, 2000, p. 259-266.
Helm, Birgit et al., "The mast cell binding site on human immunoglobulin E", Nature, vol. 331, Jan. 14, 1988, p. 180-183.
Horn, Michael et al., "Conditional autoimmunity mediated by human natural anti-FcεRIα autoantibodies?", The FASEB Journal, vol. 15, Oct. 2001, p. 2268-2274.
Horn, Michael et al., "Human anti-FcεRIα autoantibodies isolated from healthy donors cross-react with tetanus toxoid", Eur. J. Immunol., 29(4), 1999, p. 1139-1148.
Miescher, Sylvia et al., "Natural anti-FcεRIα autoantibodies isolated healthy donors and chronic idiopathic urticaria patients reveal a restricted repertoire and autoreactivity on human basophils", Human Antibodies, 10, 2001, p. 119-126.
Presta, Leonard et al., "Humanization of an Antibody Directed Against IgE", The Journal of Immunology, vol. 151, No. 5, Sep. 1, 1993, p. 2623-2632.
RA, Chisei et al., "Soluble human high-affinity receptor for IgE abrogates the IgE-mediated allergic reaction", International Immunology, vol. 5, No. 1, 1993, p. 47-54.
Stadler, B.M. et al., "Cloning of Human Anti-IgE Autoantibodies and Their Role in the Regulation of IgE Synthesis", Int. Arch Allergy Immuno.l, 107(1-3), 1995, p. 48-50.
Takai, Toshiro et al., "Expression of Humanized Fab Fragments That Recognize the IgE-Binding Domain of Human FcεRIα in COS and CHO Cells", J. Biochem. (Tokyo), vol. 129, 2001, p. 5-12.
Takai, Toshiro et al., "Production of Humanized Antibody against Human High-affinity IgE Receptor in a Serum-free Culture of CHO Cells, and Purification of the Fab Fragments", Biosci. Biotechnol. Biochem., 65(5), 2001, p. 1082-1089.
Vogel, Monique et al., "Human anti-IgE antibodies by repertoire cloning", Eur. J. Immunol., 24(5), 1994, p. 1200-1207.
Kipriyanov S M et al "Generation of Recombinant Antibodies" Molecular Biotechnology (Sep. 1999) vol. 12, No. 2, pp. 173-201.
Little M et al "Of mice and men: Hybridoma and recombinant antibodies" Immunology Today 2000 United Kingdom (2000) vol. 21, No. 8, pp. 364-370.
Nechanksy Andreas et al "The membrane-proximal part of FcepsilonRIalpha contributes to human IgE and antibody binding—implications for a general structural motif in Fc receptors" FEBS Letters vol. 441, No. 2, (Dec. 18, 1998) pp. 225-230.
Nissim A et al "The use of mouse/human IgE chimera to map the Fc-epsilon-R binding site of IgE" Methods: A Companion to Methods in Enzymology, Academic Press Inc (1995) vol. 8, No. 2, pp. 124-132.
Holt et al., "Domain antibodies: proteins for therapy"; Trends in Biotechnology, 2003, vol. 21 (11), pp. 484-490.
Davies et al., "Affinity improvement of single antibody VH domains: residues in all three hypervariable regions affect antigen binding", Immunotechnology, 1996, vol. 2, pp. 169-179.
Little et al., "Of mice and men: hybridoma and recombinant antibodies" Immunology Today (D15), 2000, vol. 21, pp. 364-370, p. 367, left-hand column, first para).

* cited by examiner

*Primary Examiner*—Michael Szperka
(74) *Attorney, Agent, or Firm*—Browdy and Neimark

(57) ABSTRACT

An antibody or an antibody fragment is provided that is efficacious for treating allergic diseases in which IgE is involved. A human antibody and a fragment thereof to a receptor (FcεRI) having high affinity to Fc portion of IgE was obtained using phage antibody display technique. The human anti-IgE receptor antibody and a fragment thereof of the invention has an activity to inhibit the binding between IgE and IgE receptor and hence is expected to be useful as a medicament for treating allergic diseases caused by the binding between IgE and IgE receptor.

9 Claims, 3 Drawing Sheets

SEQUENCE LISTING

<160> NUMBER OF SEQ ID NOS: 10

<210> SEQ ID NO 1
<211> LENGTH: 378
<212> TYPE: DNA
<213> ORGANISM: Human

<400> SEQUENCE: 1

```
caggtgcagc tgcaggagtg ggggggaggc ttggtccagc ctgggggtc cctgagactc    60 tcctgtgcag cctctggatt caccgtcagt agcaactaca tgagctgggt ccgccaggct   120
ccagggaagg ggctggagtg ggtctcagtt atttaccgtg gtgggagtgg tgataataca   180
tactacgcag gctccgtgaa gggccgattc accatctcca gagacaattc caagaacacg   240
gtgtatcttc aaatgaacag cctgagagct gaggacacgg ctgtgtatta ctgtgtgaga   300
tctagcgacg tgggctacgg tattctccgt gggtacatgg acgtctgggg caaagggacc   360
acggtcaccg tctcctca                                                 378
```

<210> SEQ ID NO 2
<211> LENGTH: 378
<212> TYPE: DNA
<213> ORGANISM: Human
<220> FEATURE:

<400> SEQUENCE: 2

```
cag gtg cag ctg cag gag tgg ggg gga ggc ttg gtc cag cct ggg ggg     48
Gln Val Gln Leu Gln Glu Trp Gly Gly Gly Leu Val Gln Pro Gly Gly
1               5                   10                  15 tcc ctg aga ctc tcc tgt gca gcc tct gga ttc acc gtc agt agc aac     96
Ser Leu Arg Leu Ser Cys Ala Ala Ser Gly Phe Thr Val Ser Ser Asn
            20                  25                  30 tac atg agc tgg gtc cgc cag gct cca ggg aag ggg ctg gag tgg gtc    144
Tyr Met Ser Trp Val Arg Gln Ala Pro Gly Lys Gly Leu Glu Trp Val
        35                  40                  45 tca gtt att tac cgt ggt ggg agt ggt gat aat aca tac tac gca ggc    192
Ser Val Ile Tyr Arg Gly Gly Ser Gly Asp Asn Thr Tyr Tyr Ala Gly
    50                  55                  60 tcc gtg aag ggc cga ttc acc atc tcc aga gac aat tcc aag aac acg    240
Ser Val Lys Gly Arg Phe Thr Ile Ser Arg Asp Asn Ser Lys Asn Thr
65                  70                  75                  80
```

| | | | | | | | | | | | | | | | | |
|---|---|---|---|---|---|---|---|---|---|---|---|---|---|---|---|---|
|gtg|tat|ctt|caa|atg|aac|agc|ctg|aga|gct|gag|gac|acg|gct|gtg|tat| 288|
|Val|Tyr|Leu|Gln|Met|Asn|Ser|Leu|Arg|Ala|Glu|Asp|Thr|Ala|Val|Tyr| |
| | | | |85| | | |90| | | |95| | | | |

| | | | | | | | | | | | | | | | | |
|---|---|---|---|---|---|---|---|---|---|---|---|---|---|---|---|---|
|tac|tgt|gtg|aga|tct|agc|gac|gtg|ggc|tac|ggt|att|ctc|cgt|ggg|tac| 336|
|Tyr|Cys|Val|Arg|Ser|Ser|Asp|Val|Gly|Tyr|Gly|Ile|Leu|Arg|Gly|Tyr| |
| | | |100| | | | |105| | | | |110| | | |

| | | | | | | | | | | | | | | |
|---|---|---|---|---|---|---|---|---|---|---|---|---|---|---|---|
|atg|gac|gtc|tgg|ggc|aaa|ggg|acc|acg|gtc|acc|gtc|tcc|tca| | 378|
|Met|Asp|Val|Trp|Gly|Lys|Gly|Thr|Thr|Val|Thr|Val|Ser|Ser| | |
| | | |115| | | | |120| | | | |125| | | |

<210> SEQ ID NO 3
<211> LENGTH: 321
<212> TYPE: DNA
<213> ORGANISM: Human

<400> SEQUENCE: 3
cacgttatac tgactcaacc gccctcagtg tccgtgtctc caggacagac tgccaggatc       60
ccctgttcgg gacaagacct gaccaacaaa tatgtctctt ggtatcaact gcagtcaggc      120
cagtcacctg cgctggtcat ctatgaggac tcaaagaggc cctcaggat ccctgagcgc      180 ttctctggct ccaactctgg agacacagcc actctgacca tcaccgggac ccaggctgcg      240
gatgaggctg acttttttctg tcaggcgtac gacaccaacg gttgggtgtt cggcgcaggg      300
accaagctga ccgtcctagg t                                                 321

<210> SEQ ID NO 4
<211> LENGTH: 321
<212> TYPE: DNA
<213> ORGANISM: Human

<400> SEQUENCE: 4

| | | | | | | | | | | | | | | | | |
|---|---|---|---|---|---|---|---|---|---|---|---|---|---|---|---|---|
|cac|gtt|ata|ctg|act|caa|ccg|ccc|tca|gtg|tcc|gtg|tct|cca|gga|cag| 48|
|His|Val|Ile|Leu|Thr|Gln|Pro|Pro|Ser|Val|Ser|Val|Ser|Pro|Gly|Gln| |
|1| | | |5| | | | |10| | | | |15| | |

| | | | | | | | | | | | | | | | | |
|---|---|---|---|---|---|---|---|---|---|---|---|---|---|---|---|---|
|act|gcc|agg|atc|ccc|tgt|tcg|gga|caa|gac|ctg|acc|aac|aaa|tat|gtc| 96|
|Thr|Ala|Arg|Ile|Pro|Cys|Ser|Gly|Gln|Asp|Leu|Thr|Asn|Lys|Tyr|Val| |
| | | |20| | | | |25| | | | |30| | | |

| | | | | | | | | | | | | | | | | |
|---|---|---|---|---|---|---|---|---|---|---|---|---|---|---|---|---|
|tct|tgg|tat|caa|ctg|cag|tca|ggc|cag|tca|cct|gcg|ctg|gtc|atc|tat| 144|
|Ser|Trp|Tyr|Gln|Leu|Gln|Ser|Gly|Gln|Ser|Pro|Ala|Leu|Val|Ile|Tyr| |
| | | |35| | | | |40| | | | |45| | | |

| | | | | | | | | | | | | | | | | |
|---|---|---|---|---|---|---|---|---|---|---|---|---|---|---|---|---|
|gag|gac|tca|aag|agg|ccc|tca|ggg|atc|cct|gag|cgc|ttc|tct|ggc|tcc| 192|
|Glu|Asp|Ser|Lys|Arg|Pro|Ser|Gly|Ile|Pro|Glu|Arg|Phe|Ser|Gly|Ser| |
| | |50| | | | |55| | | | |60| | | | |

| | | | | | | | | | | | | | | | | |
|---|---|---|---|---|---|---|---|---|---|---|---|---|---|---|---|---|
|aac|tct|gga|gac|aca|gcc|act|ctg|acc|atc|acc|ggg|acc|cag|gct|gcg| 240|
|Asn|Ser|Gly|Asp|Thr|Ala|Thr|Leu|Thr|Ile|Thr|Gly|Thr|Gln|Ala|Ala| |
|65| | | | |70| | | | |75| | | | |80| |

| | | | | | | | | | | | | | | | | |
|---|---|---|---|---|---|---|---|---|---|---|---|---|---|---|---|---|
|gat|gag|gct|gac|ttt|ttc|tgt|cag|gcg|tac|gac|acc|aac|ggt|tgg|gtg| 288|
|Asp|Glu|Ala|Asp|Phe|Phe|Cys|Gln|Ala|Tyr|Asp|Thr|Asn|Gly|Trp|Val| |
| | | |85| | | | |90| | | | |95| | | |

| | | | | | | | | | | |
|---|---|---|---|---|---|---|---|---|---|---|
|ttc|ggc|gca|ggg|acc|aag|ctg|acc|gtc|cta|ggt| 321|
|Phe|Gly|Ala|Gly|Thr|Lys|Leu|Thr|Val|Leu|Gly| |
| | | |100| | | | |105| | | |

<210> SEQ ID NO 5
<211> LENGTH: 5
<212> TYPE: PRT
<213> ORGANISM: Human
<220> FEATURE:
<223> OTHER INFORMATION: CDR1 of SEQUENCE No. 2

<400> SEQUENCE: 5

```
Ser Asn Tyr Met Ser
  1               5

<210> SEQ ID NO 6
<211> LENGTH: 19
<212> TYPE: PRT
<213> ORGANISM: Human
<220> FEATURE:
<223> OTHER INFORMATION: CDR2 of SEQUENCE No. 2

<400> SEQUENCE: 6

Val Ile Tyr Arg Gly Gly Ser Gly Asp Asn Thr Tyr Tyr Ala Gly Ser
  1               5                  10                  15

Val Lys Gly

<210> SEQ ID NO 7
<211> LENGTH: 15
<212> TYPE: PRT
<213> ORGANISM: Human
<220> FEATURE:
<223> OTHER INFORMATION: CDR3 of SEQUENCE No. 2

<400> SEQUENCE: 7

Ser Ser Asp Val Gly Tyr Gly Ile Leu Arg Gly Tyr Met Asp Val
  1               5                  10                  15

<210> SEQ ID NO 8
<211> LENGTH: 11
<212> TYPE: PRT
<213> ORGANISM: Human
<220> FEATURE:
<223> OTHER INFORMATION: CDR1 of SEQUENCE No. 4

<400> SEQUENCE: 8

Ser Gly Gln Asp Leu Thr Asn Lys Tyr Val Ser
                  5                  10

<210> SEQ ID NO 9
<211> LENGTH: 7
<212> TYPE: PRT
<213> ORGANISM: Human
<220> FEATURE:
<223> OTHER INFORMATION: CDR2 of SEQUENCE No. 4

<400> SEQUENCE: 9

Glu Asp Ser Lys Arg Pro Ser
                  5

<210> SEQ ID NO 10
<211> LENGTH: 9
<212> TYPE: PRT
<213> ORGANISM: Human
<220> FEATURE:
<223> OTHER INFORMATION: CDR3 of SEQUENCE No. 4

<400> SEQUENCE: 10

Gln Ala Tyr Asp Thr Asn Gly Trp Val
                  5
```

HUMAN TYPE ANTIHUMAN IGE RECEPTOR ANTIBODY AND FRAGMENT

TECHNICAL FIELD

The present invention relates to a human anti-IgE receptor antibody and a fragment thereof, said antibody inhibiting the binding between IgE and IgE receptor. Said antibody and fragment thereof is expected to be useful as a medicament for treating allergic diseases caused by the binding between IgE and IgE receptor.

BACKGROUND ART

Fcε receptor I (hereinafter also referred to as "FcεRI"), one of receptors (FcεR) for Fc portion (Fcε) of immunoglobulin E (IgE), has high affinity to IgE. FcεRI is a glycoprotein molecule expressed principally on the cellular membrane of mast cells and basophiles and plays an important role in type I allergic reaction for activation of these cells. Upon crosslinkage of antigen-specific IgE with corresponding multivalent antigens, i.e. allergens, FcεRI aggregates and signal transduction mechanism begins to act to thereby activate mast cells. As a result, a cellular degranulation occurs to thereby release chemical mediators such as histamine and serotonin, inducing novel synthesis and release of leukotrienes, prostaglandins and the like to provoke type I allergic reaction.

Human FcεRI consists of three distinct subunits, i.e. an IgE binding factor α chain, a signal amplifying factor β chain, and a signal transmitting factor Y chain, forming either a tetramer consisting of each one α and β chains and two Y chains, or a trimer consisting of one α chain and two Y chains.

On the surface of the cellular membrane of mast cells and basophiles, tetrameric FcεRI is principally expressed and plays an important role in type I allergic reaction for activation of these cells as described above.

On the cellular membrane of skin Langerhans cells, monocytes, eosinophiles, dendritic cells, and platelets, expression of trimeric FcεRI is principally observed though at a lower level than that of tetrameric FcεRI and is suggested to contribute to antigen display and production of chemical mediators.

It is believed that the a chain alone in FcεRI directly interacts with IgE and its binding region to IgE spans overall the extracellular region of the α chain (Nature, vol. 406 (2000), p. 259).

As for function of FcεRI within the living body, analysis with the α chain-knockout mouse suggested that FcεRI may contribute to protection mechanism from infection with certain parasite. However, a phenotype is not found under normal conditions in the knockout mouse and hence an FcεRI gene is not a gene indispensable to survival in mice.

As described above, interaction between IgE and FcεRI is important for onset of disease in case of allergic diseases. It is also known that FcεRI-expressing cells increase in patient blood. Besides, it is known that expression of FcεRI is enhanced in eosinophiles, monocytes and basophiles in peripheral blood of patients suffering from atopic asthma, allergic rhinitis and atopic dermatitis, suggesting its involvement in onset of diseases.

It is reported that autoantibody against FcεRI α chain occurs in serum from some patients with chronic hives. Thus, activation of FcεRI-expressing cells due to crosslinkage of FcεRI with anti-FcεRI autoantibody has been postulated as a mechanism for onset of disease.

DISCLOSURE OF THE INVENTION

For treating type I allergy, an antihistamine or an anti-inflammatory drug such as a steroid has widely been used. However, the conventional drugs have many disadvantages such as insufficient efficacy or adverse side effects. Therefore, a medicament that specifically inhibits the binding between IgE and FcεRI, said binding being the most important reaction in type I allergy, is expected to provide specific and fundamental efficacy while adverse side effect is reduced.

A candidate inhibitor to the binding between IgE and FcεRI includes an anti-human FcεRI antibody (J. Biochem. (Tokyo), vol. 129 (2001), p. 5), a soluble human FcεRI α chain (Int. Immunol., vol. 5 (1993), p. 47), a human IgE constant region (Fcε) (Nature, vol. 331 (1998), p. 180), an anti-human IgE antibody (J. Immunol., vol. 151 (1993), p. 2623), and the like, some of which is under actual development.

Among the candidates described above, an anti-human FcεRI antibody specifically binds to FcεRI but not to other IgE-binding molecules, thus specifically inhibiting activation of FcεRI-expressing cells due to the IgE binding. An anti-human FcεRI antibody is also expected to inhibit activation of FcεRI-expressing cells by anti-FcεRI autoantibody. Moreover, an anti-human FcεRI antibody is capable of deliver drugs specifically to FcεRI-expressing cells. From these respects, an anti-human FcεRI antibody is superior to other candidates of IgE-FcεRI binding inhibitor.

For an antibody to human FcεRI, a mouse monoclonal antibody (Japanese patent publication No. 252988/1993), a humanized antibody, a semi-chimeric and chimeric antibodies (Japanese patent publication No. 191886/1997) are known.

When an antibody is used for treatment, an antibody molecule containing mouse-derived sequences may induce production of a human anti-mouse antibody within the living body of human due to its immunogenicity, which not only negates the expected efficacy but also brings patients into threat of adverse side effects such as anaphylactic shock when frequently administered.

The humanized antibody described above is one prepared by humanizing a mouse monoclonal antibody and has a reduced immunogenicity. However, CDR regions of said humanized antibody are derived from mice and hence risk of immunogenicity and adverse side effects still remains.

Accordingly, it is desired to obtain and develop a completely human antibody or fragment thereof that is expected to avoid the risk described above to provide specific treating efficacy alone, but no such antibody or fragment thereof has hitherto been reported.

Under the circumstances, the present inventors obtained a single-chain Fv (scFv) molecule of completely human anti-human FcεRI antibody using phage antibody display technique and identified VH and VL chains of said antibody. The present inventors further analyzed property of scFv to reveal that said scFv specifically binds with FcεRI α chain, exhibits an inhibitory activity to the IgE-FcεRI binding, and inhibits histamine release from leucocytes caused by IgE-FcεRI interaction.

BEST MODE FOR CARRYING OUT THE INVENTION

Figure 1:
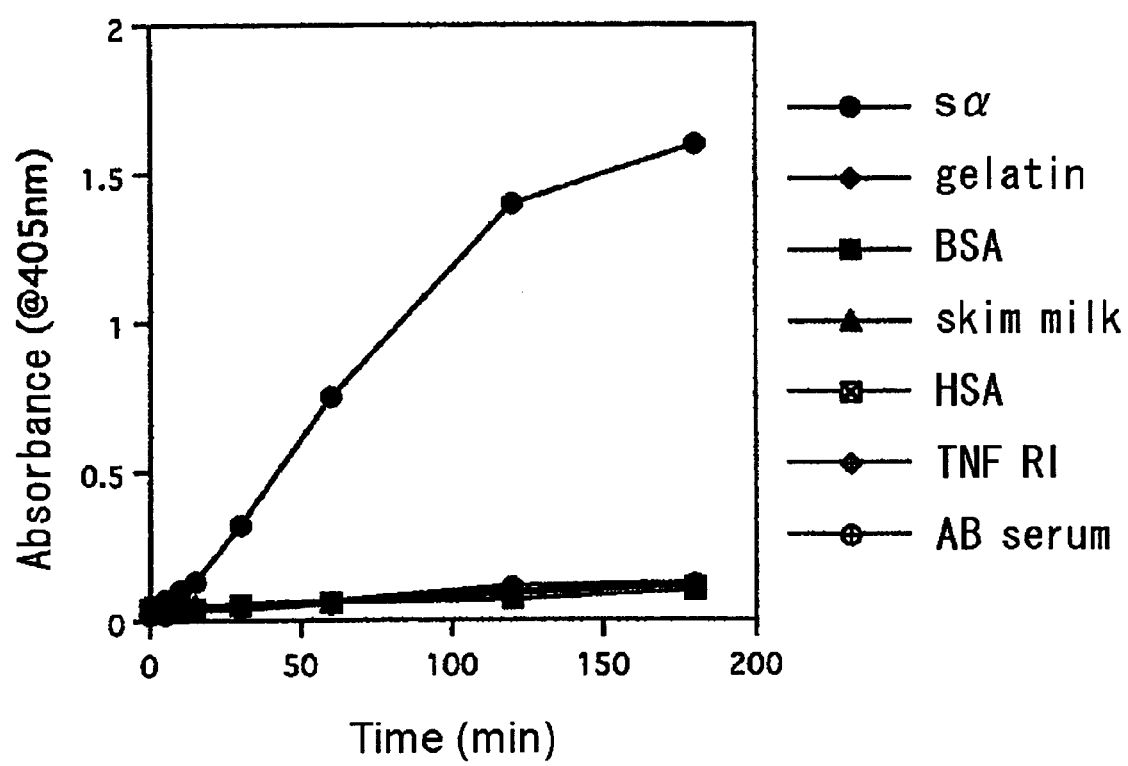
FIG. 1 shows reactivity of the obtained scFv clone (αFcR51) with various antigens (human FcεRI α chain, human serum albumin, human TNFRI, or human serum) as measured in ELISA.

Immunoglobulin heavy (H) chain and light (L) chain cDNAs were amplified from peripheral B lymphocytes from twenty healthy volunteers using RT-PCR and both amplified cDNAs of H chain and L chain were linked together with a linker DNA to prepare single-chain Fv (scFv) DNAs from lymphocytes of healthy volunteers in which VH chain and VL chain are randomly combined.

The obtained scFv DNAs were incorporated into phagemid vector pCANTAB5E to prepare scFv display phage library consisting of $10^9$ clones from healthy volunteers. This library was recovered and concentrated by contacting with a soluble fragment of human FcεRI α chain immobilized on a solid phase and phage clone displaying anti-human FcεRI α chain scFv was screened. As a result, the screened scFv clone inhibited the IgE-FcεRI binding.

VH chain and VL chain of the scFv clone with the inhibitory activity had the amino acid sequence and the nucleotide sequence coding therefor as follows:

```
[VH chain]
CAG GTG CAG CTG CAG GAG TGG GGG GGA GGC TTG GTC CAG CCT GGG GGG     48   (SEQ ID NOs: 1 and 2)
Gln Val Gln Leu Gln Glu Trp Gly Gly Gly Leu Val Gln Pro Gly Gly
 1               5                  10                  15

TCC CTG AGA CTC TCC TGT GCA GCC TCT GGA TTC ACC GTC AGT AGC AAC     96
Ser Leu Arg Leu Ser Cys Ala Ala Ser Gly Phe Thr Val Ser Ser Asn
                20                  25                  30

TAC ATG AGC TGG GTC CGC CAG GCT CCA GGG AAG GGG CTG GAG TGG GTC     144
Tyr Met Ser Trp Val Arg Gln Ala Pro Gly Lys Gly Leu Glu Trp Val
        35                  40                  45

TCA GTT ATT TAC CGT GGT GGG AGT GGT GAT AAT ACA TAC TAC GCA GGC     192
Ser Val Ile Tyr Arg Gly Gly Ser Gly Asp Asn Thr Tyr Tyr Ala Gly
50                  55                  60

TCC GTG AAG GGC CGA TTC ACC ATC TCC AGA GAC AAT TCC AAG AAC ACG     240
Ser Val Lys Gly Arg Phe Thr Ile Ser Arg Asp Asn Ser Lys Asn Thr
65                  70                  75                  80

GTG TAT CTT CAA ATG AAC AGC CTG AGA GCT GAG GAC ACG GCT GTG TAT     288
Val Tyr Leu Gln Met Asn Ser Leu Arg Ala Glu Asp Thr Ala Val Tyr
                85                  90                  95

TAC TGT GTG AGA TCT AGC GAC GTG GGC TAC GGT ATT CTC CGT GGG TAC     336
Tyr Cys Val Arg Ser Ser Asp Val Gly Tyr Gly Ile Leu Arg Gly Tyr
                100                 105                 110

ATG GAC GTC TGG GGC AAA GGG ACC ACG GTC ACC GTC TCC TCA             378
Met Asp Val Trp Gly Lys Gly Thr Thr Val Thr Val Ser Ser
            115                 120                 125

[VL chain]
CAC GTT ATA CTG ACT CAA CCG CCC TCA GTG TCC GTG TCT CCA GGA CAG     48   (SEQ ID NOs: 3 and 4)
His Val Ile Leu Thr Gln Pro Pro Ser Val Ser Val Ser Pro Gly Gln
 1               5                  10                  15

ACT GCC AGG ATC CCC TGT TCG GGA CAA GAC CTG ACC AAC AAA TAT GTC     96
Thr Ala Arg Ile Pro Cys Ser Gly Gln Asp Leu Thr Asn Lys Tyr Val
                20                  25                  30

TCT TGG TAT CAA CTG CAG TCA GGC CAG TCA CCT GCG CTG GTC ATC TAT     144
Ser Trp Tyr Gln Leu Gln Ser Gly Gln Ser Pro Ala Leu Val Ile Tyr
            35                  40                  45

GAG GAC TCA AAG AGG CCC TCA GGG ATC CCT GAG CGC TTC TCT GGC TCC     192
Glu Asp Ser Lys Arg Pro Ser Gly Ile Pro Glu Arg Phe Ser Gly Ser
    50                  55                  60

AAC TCT GGA GAC ACA GCC ACT CTG ACC ATC ACC GGG ACC CAG GCT GCG     240
Asn Ser Gly Asp Thr Ala Thr Leu Thr Ile Thr Gly Thr Gln Ala Ala
65                  70                  75                  80

GAT GAG GCT GAC TTT TTC TGT CAG GCG TAC GAC ACC AAC GGT TGG GTG     288
Asp Glu Ala Asp Phe Phe Cys Gln Ala Tyr Asp Thr Asn Gly Trp Val
                85                  90                  95
```

```
                                                     -continued
TTC GGC GCA GGG ACC AAG CTG ACC GTC CTA GGT                          321
Phe Gly Ala Gly Thr Lys Leu Thr Val Leu Gly
                100                 105
```

Within the sequences described above, CDR1 to CDR3 of VH chain and VL chain have the amino acid sequences as follows:

```
[VH chain]
CDR1:
Ser Asn Tyr Met Ser                    (SEQ ID NO: 5)

CDR2:
Val Ile Tyr Arg Gly Gly Ser Gly        (SEQ ID NO: 6)
Asp Asn Thr Tyr Tyr Ala Gly Ser
Val Lys Gly

CDR3:
Ser Ser Asp Val Gly Tyr Gly Ile        (SEQ ID NO: 7)
Leu Arg Gly Tyr Met Asp Val

[VL chain]
CDR1:
Ser Gly Gln Asp Leu Thr Asn Lys        (SEQ ID NO: 8)
Tyr Val Ser CDR2:
Glu Asp Ser Lys Arg Pro Ser            (SEQ ID NO: 9)

CDR3:
Gln Ala Tyr Asp Thr Asn Gly Trp        (SEQ ID NO: 10)
Val
```

An antibody fragment having either or both of VH chain and VL chain as described above possesses a variable region of anti-human FcεRI antibody derived from human and strongly reacts with human FcεRI α chain to thereby inhibit the IgE-FcεRI binding.

VH chain and/or VL chain disclosed herein were obtained in the form of scFv using the phage antibody display technique. VH chain and/or VL chain according to the present invention may not only be applied to scFv but also to a complete antibody molecule in which the disclosed VH chain and/or VL chain is combined with a constant region of a human immunoglobulin, or other forms of antibody fragment in which the disclosed VH chain and/or VL chain is combined with a portion of a constant region of a human immunoglobulin such as Fab, Fab' or F(ab')$_2$, or a single-chain antibody (scAb) in which scFv is combined with a constant region of a human immunoglobulin. The present invention also encompasses a modified protein molecule in which a protein molecule of the antibody and fragments thereof as described above is bound with a modifying agent.

As described above, the human monoclonal antibody and fragment thereof of the present invention is capable of inhibiting various allergic reactions induced by the binding between IgE and FcεRI and hence may be used as a medicament for treating and preventing allergic diseases. This may suggest possibility of the human monoclonal antibody and fragment thereof of the present invention as an excellent novel anti-allergic agent that has an extremely long half-life in blood while much less likely to induce adverse side effect, which property not found in the conventional anti-allergic agents.

It is also expected that the human monoclonal antibody and fragment thereof of the present invention may be applied for the missile therapy targeting FcεR-expressing cells when combined with other antibodies or drugs.

Moreover, the human monoclonal antibody and fragment thereof of the present invention may also provide immunoassay for detecting or measuring FcεRI-expressing cells in human peripheral blood or tissues by utilizing its property.

A complex of the human monoclonal antibody and fragment thereof of the present invention with an immunosorbent consisting of immunologically inactive adsorbing material has many applications.

First, it allows for purification of FcεRI α chain on the FcεRI-expressing cells in human peripheral blood or tissues by immunoaffinity chromatography.

Besides, it is also possible to use said complex for purification of FcεRI α chain in culture supernatant produced from cultured cells that are transfected by the genetic recombination technique.

A peptide, or a derivative thereof, of a variable region of the human monoclonal antibody of the present invention also provides a means for isolating a peptide or an anti-idiotype antibody from library. The obtained peptide and anti-idiotype antibody, and a derivative thereof, may be expected to be efficacious for treating allergic diseases through neutralization of IgE, or for treating patients possessing anti-human high-affinity IgE receptor autoantibody.

Moreover, a peptide, or a derivative thereof, of a variable region of the human monoclonal antibody of the present invention may also be used for immunization of a patient to thereby induce anti-idiotype antibody, which antibody is expected to neutralize the activity of IgE antibody in blood. For this purpose, a peptide, or a derivative thereof, of a variable region of the human monoclonal antibody of the present invention may be used as a novel medicament for immune therapy, i.e. a vaccine.

The present invention is explained in more detail by means of the following Examples which are not intended to restrict a scope of the present invention in any sense.

EXAMPLE

Example 1

Construction of Phage Library from Healthy Volunteers

A phage library was constructed as reported by J. D. Marks et al., J. Mol. Biol., 222: 581-597, 1991.

Lymphocytes were separated from peripheral blood from twenty healthy volunteers using Ficoll, washed thoroughly with PBS and treated with ISOGEN (Nippon Gene Co., Ltd.) to prepare total RNAs. The obtained total RNAs were divided into four portions for preparing cDNAs with primers specific for constant regions of human IgG, IgM, κ chain and λ chain, respectively, using first strand cDNA synthesis kit (Pharmacia bio tec). Using the obtained cDNAs as a template, a polymerase chain reaction (PCR) was performed for amplification of genes encoding antibody V regions using specific primers for each combination of either VH (γ or μ) and JH, Vκ and Jκ, or Vλ and Jλ, as reported by Marks et al.

Subsequently, the resulting VH (λ or μ) and Vκ genes, and VH (γ or μ) and Vλ genes, were linked together, respectively, by assembly PCR using a linker DNA to prepare single-chain scFv DNAs. The obtained scFv DNAs were further modified by PCR to add NotI and SfiI restriction sites, elecrophoresed on agarose gel and then purified. The purified scFv DNAs were digested with restriction enzymes SfiI (Takara) and NotI (Takara) and then cloned into phagemid pCANTAB5E (Pharmacia). The phagemid pCANTAB5E bound with scFv DNAs of either VH(Y)-Vκ, VH(Y)-Vλ, V(μ)-Vκ, or VH(μ)-Vλ were introduced into E. coli TG1 by electroporation. Judging from the number of transfected TG1, it was estimated that VH(Y)-Vκ, VH(Y)-Vλ, V(μ)-Vκ, and VH(μ)-Vλ had diversity of $1.1\times10^8$, $2.1\times10^8$, $8.4\times10^7$, and $5.3\times10^7$ clones, respectively. With the transfected TG1, phage antibodies were expressed using M13KO7 helper phage to prepare scFv-expressing phage library from healthy volunteers.

Example 2

Screening

A soluble fragment of human IgE receptor (FcεRI) α chain (4 μg/mL) was dissolved in 0.1 M NaHCO$_3$ (1 mL) and plated on 35 mm dish (Iwaki) at 4° C. overnight for immobilization. After blocking with 1% BSA/PBS at 20° C. for 2 hours, the dish was washed six times with 0.05% Tween 20-PBS and thereto was added 0.9 mL ($1\times10^{12}$ tu/mL) of the antibody phage library (a solution of single-chain antibody display phages) from healthy volunteers. After washing the dish 10 times with 0.05% Tween 20-PBS, 0.4 mL of glycine buffer (pH 2.2) was added to elute single-chain antibody display phage that bound with FcεRI α chain. The eluted phage was infected to E. coli TG1 at logarithmic phase after adjusting pH with 1 M Tris(hydroxymethyl)aminomethane-HCl, pH 9.1. The infected TG1 cells were centrifuged at 3000×g for 5 minutes. After removal of supernatant, the remaining portions were suspended in 200 μL of 2×YT medium, plated on SOBAG plate and incubated in an incubator at 30° C. overnight. The formed colonies were added with an appropriate amount of 2×YT medium and then suspended and recovered with a scraper (Coaster). The TG1 cells (500 μL) were inoculated to 50 mL of 2×YTAG medium and rescued with a helper phage to prepare post-screening phage library. For each of phage libraries VH(Y)-Vκ, VH(Y)-Vλ, V(μ)-Vκ, and VH(μ)-Vλ from healthy volunteers, screening was performed four times. After the fourth screening, clones were arbitrarily extracted from the SOBAG plate for confirming their expression of scFv and for specificity of scFv with FcεRI α chain ELISA as well as nucleotide sequence analysis.

Example 3

FcεRI α Chain ELISA for Screening

ELISA for screening the isolated clones was performed as described below. An ELISA plate immobilized with FcεRI α chain and a control protein was used for screening. Each 40 μL/well of 2.5 μg/mL FcεRI α chain, 2.5 μg/mL human serum albumin, 2.5 μg/mL human TNFRI or human serum was placed in ELISA plate (Nunc) and the plate was left to stand at 4° C. for 16 hours for immobilization. The immobilized ELISA plate was added with 400 μL/well TBS solution containing 0.5% BSA, 0.5% gelatin and 5% skim milk and left to stand at 4° C. for 2 hours for blocking.

A sample solution (100 μL/well) containing scFv display phage was added to the plate. After reaction, the sample solution was discarded and the plate was washed five times with a washing solution. The plate was reacted with anti-M13 monoclonal antibody labeled with biotin (Pharmacia) and then with anti-mouse IgG antibody labeled with alkaline phosphatase (AP). After washing five times with a washing solution, 100 μL/well substrate solution for development (PBS solution containing 1 g/mL p-nitrophenyl phosphate (Wako) and 10% diethanolamine (Wako)) was added to the plate. The light was shielded and the substrate was developed at room temperature to 37° C. for 5 to 10 minutes. To the plate was added 50 μL/well of 1N sulfuric acid and absorbance at 405 nm was measured with Multiplate Autoreader NJ-2001 (Inter Med). As a result, all the estimated clones proved to be specific for FcεRI (FIG. 1).

Example 4

Sequence Analysis of Clones

A DNA sequence of scFv gene of the isolated clones was determined for VH and VL using Dye terminator cycle sequencing FS Ready Reaction kit (Applied Biosystems). As a result of ELISA and sequence analysis, the isolated clones were classified into four groups.

Example 5

Expression and Recovery of scFv

A soluble scFv was expressed with E. coli HB2151 and crude-purified by recovering a fraction of E. coli periplasm. If necessary, scFv was further purified by affinity purification using RPAS Purification Module (Pharmacia Biotech). Purity of the purified scFv protein was determined by SDS polyacrylamide gel electrophoresis and Western blot targeting for Etag epitope at the C terminal of scFv protein. A protein concentration of the purified scFv product was determined with Protein Assay kit (BIO-RAD).

Example 6

Measurement of Affinity of Purified scFv by SPR

Affinity of the purified scFv was measured by SPR method using BIAcore (BIAcore). As a result, a clone with the highest affinity, αFcR51, was estimated to have a dissociation constant of $0.58\times10^{-8}$ M to human FcεRI α chain.

Example 7

Experiment for Inhibition to IgF Binding to FcεRI α Chain

A clone αFcR51, which was proved to inhibit IgE binding to FcεRI by an experiment for inhibition to IgE-FcεRI binding using the purified scFv, was further analyzed in more detail.

Figure 2:
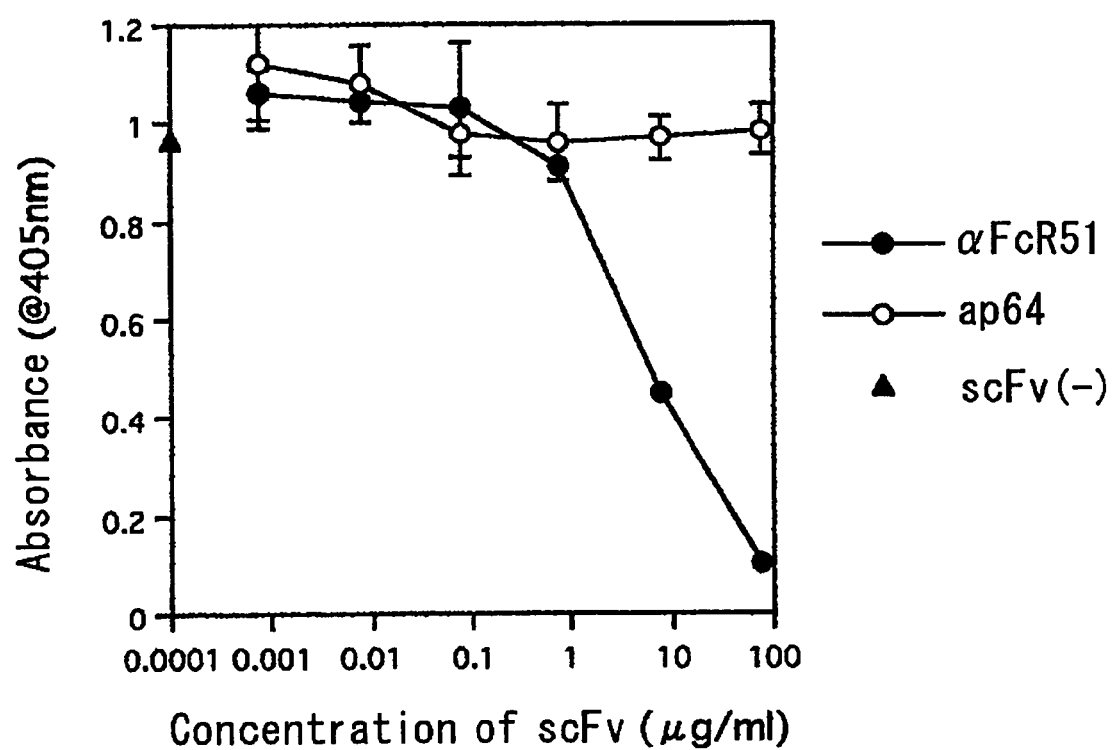
FIG. 2 shows an inhibitory activity of scFv clone (αFcR51) to the IgE-FcεRI binding as measured in ELISA.

An ELISA plate immobilized with human IgE was used for a binding inhibition experiment. 40 μL/well of human IgE (2.5 μg/mL) was placed in ELISA plate (Nunc) and the plate was left to stand at 4° C. for 16 hours for immobilization. A biotin-labeled FcεRI α chain (55 ng/mL) was reacted with αFcR51 scFv or other scFv clone (ap64) having a different specificity as a control at various concentrations and then each 40 μL/well of the reactant was added to the IgE-immobilized ELISA plate for reaction. Binding between FcεRI α chain and IgE was measured with AP-labeled streptavidin and a substrate. As a result, scFv inhibited the IgE binding to FcεRI α chain at not less than 0.1 μg/ml with the inhibition rate of 90% or more at not less than 100 μg/ml of scfv as shown in FIG. 2.

Example 8

Experiment for Inhibition to Histamine Release

Figure 3:
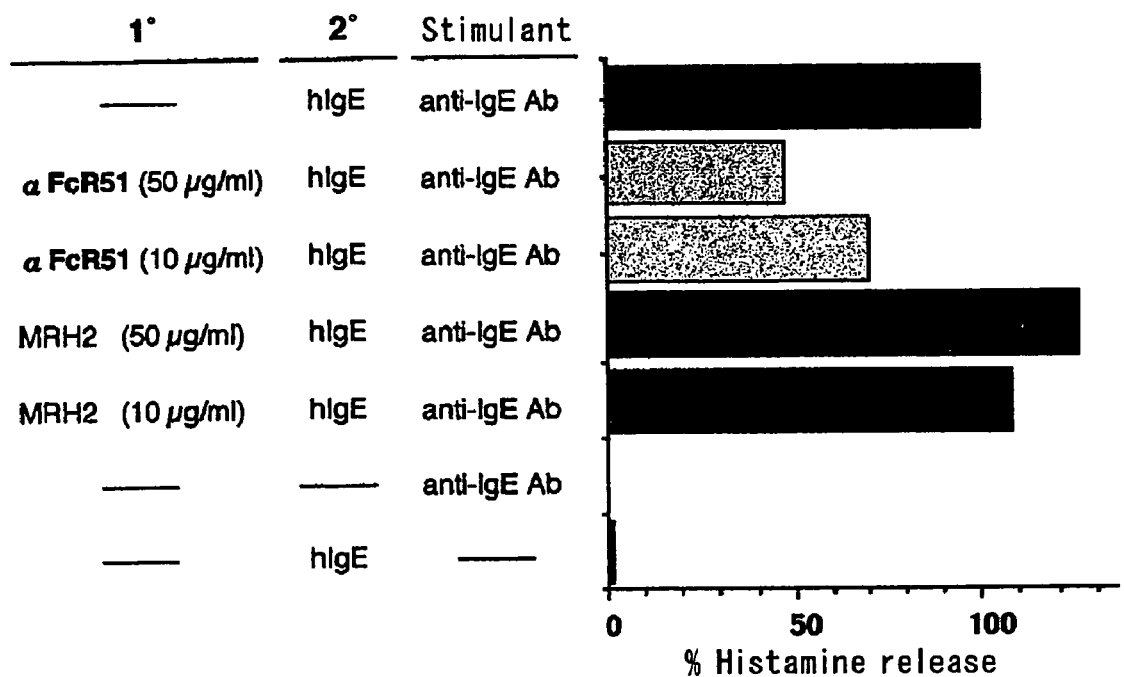
FIG. 3 shows an inhibitory effect of scFv clone (αFcR51) to histamine release by inhibiting the IgE-FcεRI binding.

Leucocytes ($10^6$ cells) were prepared from peripheral blood and treated with a lactate buffer to remove IgE on the surface of the cells. The resulting leucocytes were reacted with αFcR51 scFv or other scFv clone (MRH2) having a different specificity as a control on ice for 15 minutes. After adding IgE at a final concentration of 25 μg/ml, the mixture was further reacted on ice for 15 minutes. After washing, the cells ($2 \times 10^5$) were added to a plate coated with anti-human IgE ascites (Sigma) for reaction at 37° C. for 30 minutes. A supernatant was recovered and determined for histamine release with a histamine kit (Eiken Chemical Co., Ltd.). As a result, αFcR51 was proved to inhibit histamine release in a concentration-dependant manner as shown in FIG. 3.

The human anti-human IgE receptor antibody and a fragment thereof of the present invention neutralizes the IgE binding activity of human IgE receptor and hence may be used as a medicament for treating allergic diseases caused by the binding between IgE and IgE receptor. It is also expected that the human anti-human IgE receptor antibody and a fragment thereof of the present invention may be applied to a missile therapy targeting IgE receptor-expressing cells. The human anti-human IgE receptor antibody and a fragment thereof of the present invention may also be used for detection and determination of IgE receptor expressed on the cellular surface or for isolation and purification of IgE receptor or IgE receptor-expressing cells, and as a reagent for research or a reagent for monitoring patients.

Moreover, the human antibody and a fragment thereof of the present invention or a derivative thereof allows for isolation of a peptide to be an antigenic epitope as well as isolation or induction of anti-idiotype antibody. The resulting peptide and anti-idiotype antibody or a derivative thereof is expected to be efficacious for treating allergic diseases through IgE neutralization or for treating patients possessing anti-human IgE receptor autoantibody.

---

The invention claimed is:

1. A human anti-human Fcε receptor I (hereinafter referred to as "FcεRI") antibody or an antibody fragment thereof that binds to a human FcεRI and has an activity to inhibit the binding between the FcεRI and IgE and that is prepared by the genetic recombination technique with an expression vector in which the following gene fragments are incorporated;

a) a gene fragment encoding VH chain of the human anti-human FcεRI antibody, wherein complimentary determining regions (CDR1 to CDR3) in said VH chain have the following amino acid sequences;
CDR1: Ser Asn Tyr Met Ser (SEQ ID NO: 5);
CDR2: Val Ile Tyr Arg Gly Gly Ser Gly Asp Asn Thr Tyr Tyr Ala Gly Ser Val Lys Gly (SEQ ID NO: 6);
CDR3: Ser Ser Asp Val Gly Tyr Gly Ile Leu Arg Gly Tyr Met Asp Val (SEQ ID NO: 7), and
b) a gene fragment encoding VL chain of the human anti-human FcεRI antibody, wherein complementary determining regions (CDR1 to CDR3) in said VL chain have the following amino acid sequences;
CDR1: Ser Gly Gln Asp Leu Thr Asn Lys Tyr Val Ser (SEQ ID NO: 8);
CDR2: Glu Asp Ser Lys Arg Pro Ser (SEQ ID NO: 9);
CDR3: Gln Ala Tyr Asp Thr Asn Gly Trp Val (SEQ ID NO: 10)

2. The human anti-human FcεRI antibody or the antibody fragment thereof of claim 1 wherein said VH chain gene consists of a nucleotide sequence encoding the amino acid sequence as set forth in SEQ ID NO: 2, and said VL chain gene consists of a nucleotide sequence encoding the amino acid sequence as set forth in SEQ ID NO: 4.

3. The human anti-human FcεRI antibody or the antibody fragment thereof of claim 1 wherein a single-chain Fv gene comprising said gene fragment encoding VH chain bound to said gene fragment encoding VL chain is incorporated in the expression vector.

4. The human anti-human FcεRI antibody or the antibody fragment thereof of claim 1 wherein said gene fragment encoding VH chain and said gene fragment encoding VL chain are bound to a human antibody CH chain gene and a human antibody CL chain gene, respectively.

5. The human anti-human FcεRI antibody or the antibody fragment thereof of claim 1 wherein said gene fragment encoding VH chain and said gene fragment encoding VL chain are bound to a human antibody CH chain gene or a portion thereof and a human antibody CL chain gene or a portion thereof, respectively.

6. The human anti-human FcεRI antibody or the antibody fragment thereof of claim 1 wherein said antibody fragment is selected from Fab, Fab', or F (ab')$_2$.

7. The human anti-human FcεRI antibody or the antibody fragment thereof of claim 1 wherein a single-chain Fv gene comprising said gene fragment encoding VH chain bound to said gene fragment encoding VL chain is incorporated in the expression vector, said single-chain Fv gene being bound to a human antibody CH chain gene or a portion thereof or a human antibody CL chain gene or a portion thereof.

8. An inhibitor to the IgE-IgE receptor binding comprising the human anti-IgE receptor antibody or the human anti-IgE receptor antibody fragment of claim 1.

9. A medicament for treating allergic diseases comprising the human anti-IgE receptor antibody fragment of claim 1, wherein said antibody fragment is in the form of scFv, Fab or Fab'.

* * * * *